(12) United States Patent
Livingston et al.

(10) Patent No.: US 10,888,426 B2
(45) Date of Patent: Jan. 12, 2021

(54) MULTI-LAYER SUBSTRATE APPARATUS, SYSTEMS AND METHODS OF ASSEMBLING SAME

(71) Applicant: The Aerospace Corporation, El Segundo, CA (US)

(72) Inventors: Frank Edward Livingston, Redondo Beach, CA (US); Timothy Ganey, Tampa, FL (US)

(73) Assignee: The Aerospace Corporation, El Segundo, CA (US)

( * ) Notice: Subject to any disclaimer, the term of this patent is extended or adjusted under 35 U.S.C. 154(b) by 88 days.

(21) Appl. No.: 16/212,638

(22) Filed: Dec. 6, 2018

(65) Prior Publication Data
US 2020/0179119 A1 Jun. 11, 2020

(51) Int. Cl.
*A61F 2/28* (2006.01)
*B32B 3/30* (2006.01)
*A61F 2/30* (2006.01)

(52) U.S. Cl.
CPC ............ *A61F 2/28* (2013.01); *A61F 2/30771* (2013.01); *B32B 3/30* (2013.01); *A61F 2002/286* (2013.01); *A61F 2002/2817* (2013.01); *A61F 2002/2821* (2013.01); *A61F 2002/30079* (2013.01); *A61F 2002/30087* (2013.01); *B32B 2250/05* (2013.01); *B32B 2307/202* (2013.01); *B32B 2307/208* (2013.01); *B32B 2457/00* (2013.01); *B32B 2535/00* (2013.01)

(58) Field of Classification Search
CPC .... A61F 2210/0016; A61F 2310/00329; A61F 2310/00928; A61F 2/28; A61F 3/30771; A61F 2002/2817; A61F 2002/2821; B32B 3/30
See application file for complete search history.

(56) References Cited

U.S. PATENT DOCUMENTS 7,526,357 B2   4/2009   Livingston et al.

OTHER PUBLICATIONS

M. Telford, "The Case for Bulk Metallic Glass," Materials Today, Mar. 2004, pp. 36-43.

*Primary Examiner* — Jason-Dennis N Stewart
(74) *Attorney, Agent, or Firm* — Duane Morris, LLP

(57) ABSTRACT

A multi-layer substrate apparatus includes a first layer configured to provide at least one electrical-based property. A second layer proximate to the first layer is configured to provide at least one mechanical-based property. A third proximate to the second layer includes at least one chemical component such that the third layer is enabled to regulate the multi-layer substrate apparatus based on a system that the multi-layer substrate apparatus is being used with. A fourth layer proximate to the third layer is configured to provide at least one magnetic-based property. A fifth layer proximate to the fourth layer is configured to provide support based on the system that the multi-layer substrate apparatus is being used with. The fifth layer includes a geometric portion that is configured to facilitate at least one process therein.

23 Claims, 5 Drawing Sheets

MULTI-LAYER SUBSTRATE APPARATUS, SYSTEMS AND METHODS OF ASSEMBLING SAME

BACKGROUND

At least some known devices, such as medical implant devices or other interbody devices, can be used in systems, such as the human body. Such devices can include materials that are single phase and single function to treat, for example, the cell surface interface, with the particular intent of improving acceptance by the system, enhancing fixation therein, and/or minimizing infection. The devices can include materials that are non-graded and compositionally pure, and are designed for specific application, such as spinal adjuncts, knee and hip replacements, and bone fillers. At least some known devices, such as implant devices, can seek to replicate the form and mechanical compliance of natural biological materials to provide a relatively inert system to ensure biocompatibility and avoid unsolicited cell interactions and physiological response. However, such devices are limited in their physiological capability. Moreover, the biomimetic functionality of known implantable devices can be limited. For example, such devices can be singular with respect to phase and function.

BRIEF DESCRIPTION

The embodiments described herein provide a multi-layer substrate apparatus that is multi-functional and has multiple phases; thereby having the ability to control various different aspects of the behavior of the system it is being used with, such as being able to control various different aspects of cell-surface behavior, such as adhesion, motility, proliferation and differentiation. For example, in some embodiments, a multi-layer substrate apparatus is provided that includes a first layer that is configured to provide at least one electrical-based property. A second layer is positioned proximate to the first layer, wherein the second layer is configured to provide at least one mechanical-based property. A third layer is positioned proximate to the second layer, wherein the third layer includes at least one chemical component such that the third layer is enabled to regulate the multi-layer substrate apparatus based, at least in part, on a system that the multi-layer substrate apparatus is being used with. A fourth layer is positioned proximate to the third layer, wherein the fourth layer is configured to provide at least one magnetic-based property. A fifth layer is positioned proximate to the fourth layer, wherein the fifth layer is configured to provide support based, at least in part, on the system that multi-layer substrate apparatus is being used with. The fifth layer includes a geometric portion that is configured to facilitate at least one process therein.

In other embodiments, a system is provided, wherein the system includes at least one portion having a cavity defined therein. The system also includes a multi-layer substrate apparatus that is positioned in the cavity, wherein the multi-layer substrate includes a first layer that is configured to provide at least one electrical-based property and a second layer positioned proximate to the first layer, wherein the second layer is configured to provide at least one mechanical-based property. A third layer is positioned proximate to the second layer, wherein the third layer includes at least one chemical component such that the third layer is enabled to regulate the multi-layer substrate apparatus based, at least in part, on the portion. A fourth layer is positioned proximate to the third layer, wherein the fourth layer is configured to provide at least one magnetic-based property. A fifth layer is positioned proximate to the fourth layer, wherein the fifth layer is configured to provide support based, at least in part, on the portion. The fifth layer includes a geometric portion that is configured to facilitate at least one process therein.

In some embodiments, a method of assembling a multi-layer substrate apparatus is provided. The method includes providing a first layer that is configured to provide at least one electrical-based property. A second layer is positioned proximate to the first layer, wherein the second layer is configured to provide at least one mechanical-based property. A third layer is positioned proximate to the second layer, wherein the third layer comprises at least one chemical component such that the third layer is enabled to regulate the multi-layer substrate apparatus based, at least in part, on a system that the multi-layer substrate apparatus is being used with. A fourth layer is positioned proximate to a third layer, wherein the fourth layer is configured to provide at least one magnetic-based property. A fifth layer is positioned proximate to the fourth layer, wherein the fifth layer is configured to provide support based, at least in part, on the system that the multi-layer substrate apparatus is being used with. At least one process is facilitated within the fifth layer using a geometric portion defined within the fifth layer.

DETAILED DESCRIPTION

Figure 1:
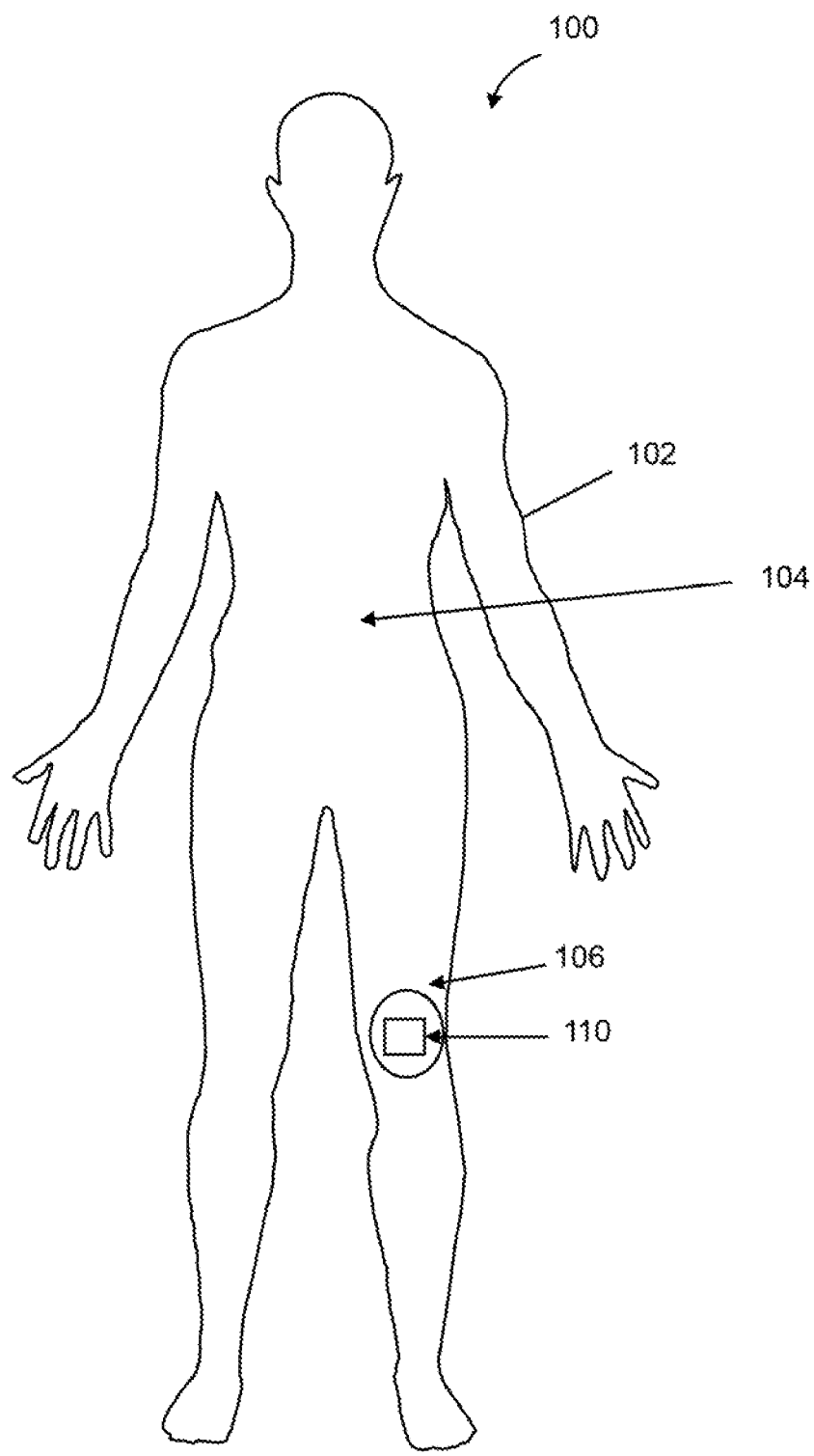
FIG. 1 is a block diagram of a portion of an exemplary system in accordance with some embodiments of the present disclosure.

FIG. 1 illustrates a portion of an exemplary system 100. In some embodiments, system 100 can be a mammal, such as a human. System 100 can have various components and component layers, such as an outer skin tissue layer 102 that encloses an internal portion 104 of system 100. Internal portion 104 of system 100 can include a plurality of skeletal bones (not shown) that are connected to one another. It should be noted that the present disclosure is not limited to humans and one of ordinary skill in the art will appreciate that the current disclosure may be used in connection with other types of systems. For example, in some embodiments, system 100 can be space, military, and defense technology systems.

In some embodiments, a cavity 106 can be defined within a bone structure (not shown) such that a multi-layer substrate apparatus 110 can be positioned within cavity 106. For example, healthcare providers can create cavity 106 using suitable surgical tools and can position multi-layer substrate apparatus 110 within cavity 106.

As described in more detail below, multi-layer substrate apparatus 110 is a multi-phase and multi-functional device that can be used in systems, such as system 100, wherein apparatus 110 is enabled to facilitate control, such as cellular control. Multi-layer substrate apparatus 110, in some embodiments, can be a polylaminate material differentiation platform that has layered multi-constituent, multi-phase architectures that are designed to regulate various stages of, for example, implant integration. Apparatus 110 combines hybrid (amalgam) material systems and laser-modified chemical and physical structuring to enable the creation of engineered inhomogeneities or composition inclusions with the architecture or bio-architecture. For example, the variegated domains can be patterned and ordered to achieve biomimetic instructions that are mapped spatially and temporally to biological or physiological states. The resonance provides the ability to prepare new hierarchical structures, enabling cell control through both cooperative networks and autonomous channels.

Figure 2A:
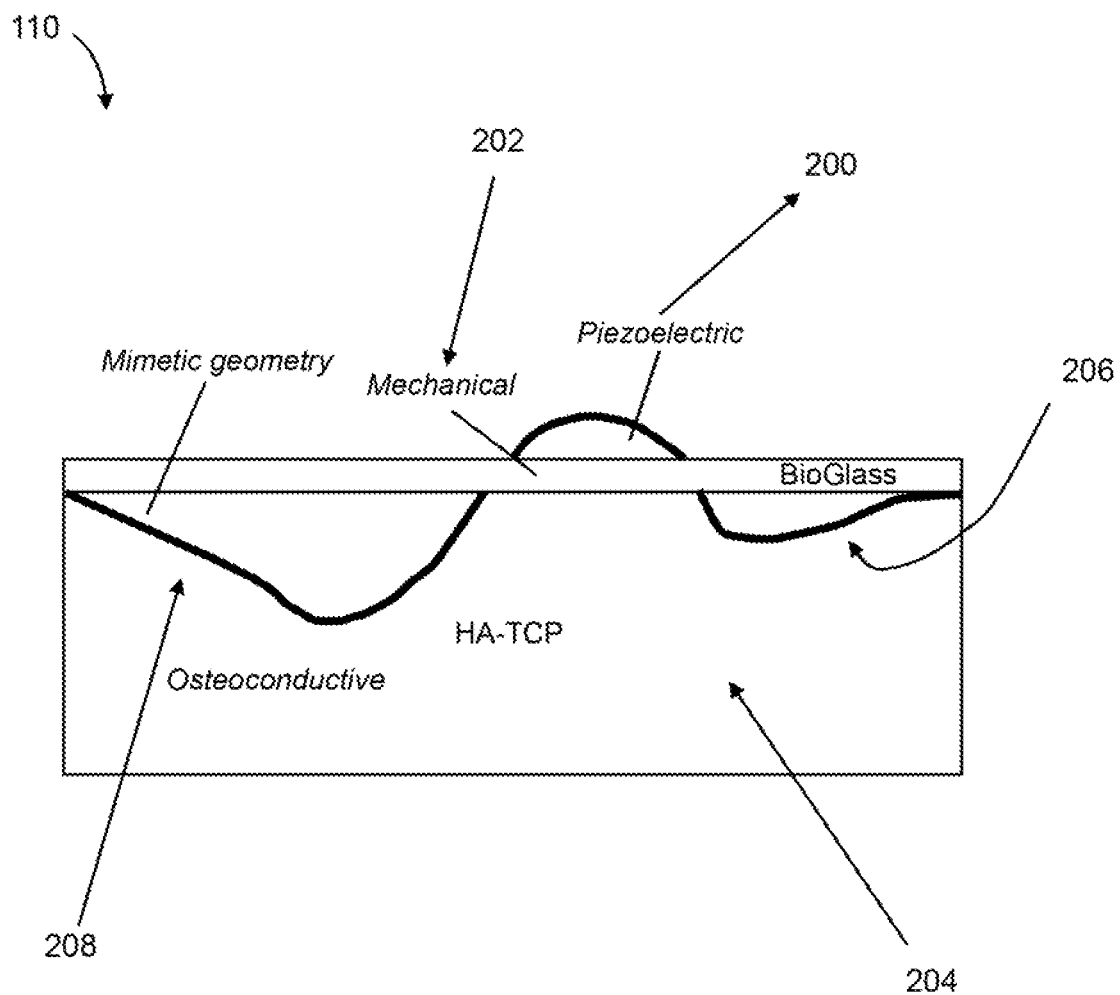
FIG. 2A is a side view of the multi-layer substrate apparatus shown in FIG. 1, in accordance with some embodiments of the present disclosure.

FIG. 2A is an exemplary side view of multi-layer substrate apparatus 110. In some embodiments, apparatus 110 includes a first layer 200 that is configured to provide at least one electrical-based property. The electrical-based property can be an electrical conduction source, an electron transfer source, and/or an electrical induction source. For example, as shown in FIG. 2A, first layer 200 can provide electrical inductions, such as piezoelectric behavior. A second layer 202 is positioned proximate to first layer 200. In some embodiments, second layer 202 is configured to provide at least one mechanical-based property, which can include a compliance property, a rigidity property, and/or a torsional property. For example, in some embodiments, second layer 202 can include a glass material or an allograft material.

In some embodiments, a third layer 204 is positioned proximate to second layer 202, wherein third layer 204 includes at least one chemical component such that third layer 204 is enabled to regulate multi-layer substrate apparatus 110 based, at least in part, on a system, such as system 100, that apparatus 110 is being used with. As such, the chemistry, phase, and composition of third layer 204 can be defined to regulate application-specific behavior. For example, as shown in FIG. 2A, third layer 204 can include tricalcium phosphate/hydroxyapatite that can enable apparatus 110 to biochemically combine with, for example, a bone structure, and emulate bone growth within the bone structure.

A fourth layer 206 is positioned proximate to third layer 204, wherein fourth layer 206 is configured to provide at least one magnetic-based property. For example, fourth layer 206 can include a metal layer and/or metal component. The metal layer can have a predefined magnetic strength and magnetic response that can be tailored to regulate and respond to application specific processes. For example, the metal layer can be defined based on the system, such as system 100, that apparatus 110 is being used with.

In some embodiments, a fifth layer 208 is positioned proximate to fourth layer 206, wherein fifth layer is configured to provide support based, at least in part, on the system, such as system 100, that multi-layer substrate apparatus 110 is being used with. In some embodiments, fifth layer 208 includes a geometric portion that is configured to facilitate at least one process therein. For example, fifth layer 208 can align architectural form with intended function of apparatus 110 within the system, such as system 100, that apparatus 110 is being used with. Fifth layer 208 can also have, in some embodiments, a mimetic geometry layer for controlling application-specific tasks, and can be configured to adapt and respond to variable environments of the system, such as system 100, that apparatus 110 is being used with. The mimetic geometry layer can include at least one pattern defined thereon and the mimetic geometry can communicate with first layer 200, second layer 202, third layer 204, and/or fourth layer 206.

When apparatus 110 is positioned within a system, such as system 100, first layer 200, second layer 202, third layer 204, fourth layer 206, and/or fifth layer 208 can act autonomously to facilitate and accomplish individual discrete functions, or they can operate cooperatively to regulate multiple interrelated processes. As such, apparatus 110 is a multi-material, multi-interface, multi-functional apparatus that can be pre-programmed for application-specific tasks, and can be designed to adapt and respond to variable environments. Moreover, in some embodiments, there can be interfaces (not shown), or regions between first layer 200, second layer 202, third layer 204, fourth layer 206, and/or fifth layer 208 that can control various processes, such as cell proliferation, differentiation and phenotype expression for stem cell control, infrared photon detection and pyroelectric response for thermal sensors, acoustic and long-wave detection for communication devices, and photon capture and storage for energy-harvesting devices.

Figure 2B:
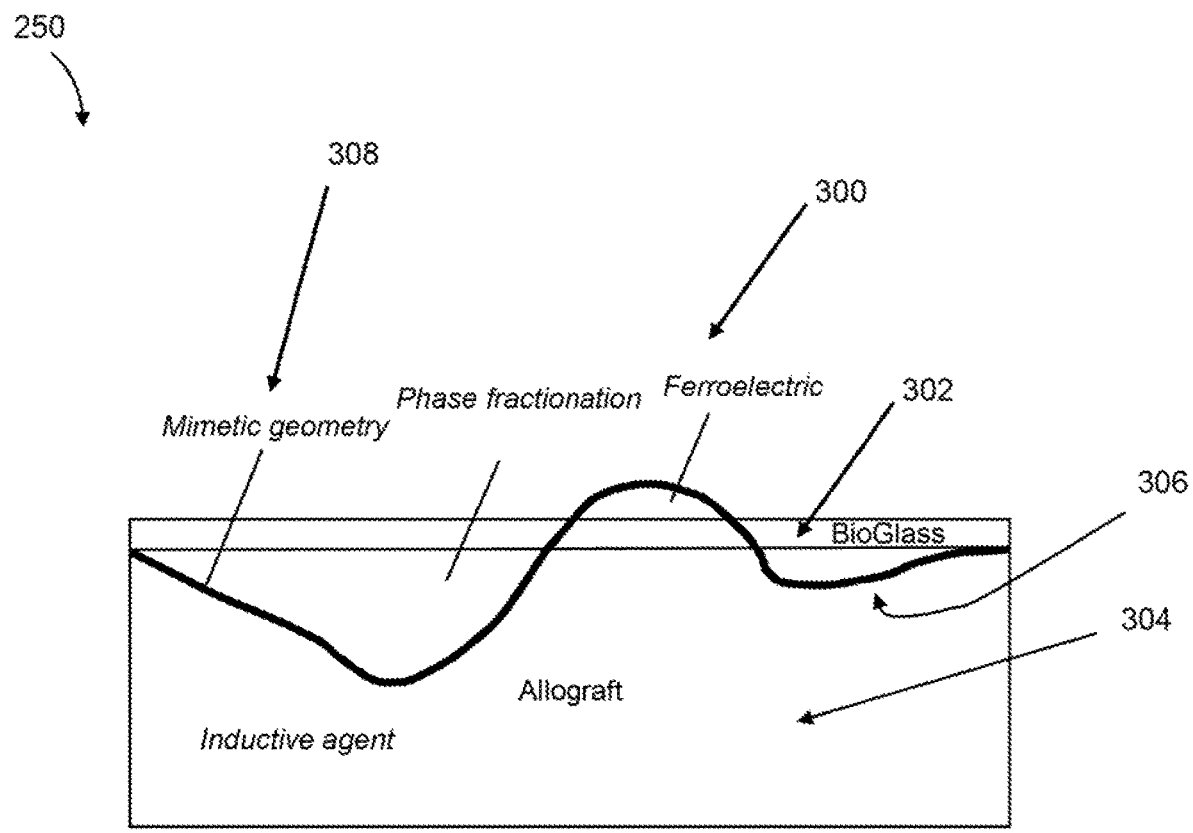
FIG. 2B is a side view of an alternative multi-layer substrate apparatus that can be used with the system shown in FIG. 1, in accordance with some embodiments of the present disclosure.

FIG. 2B is an exemplary side view of an alternative multi-layer substrate apparatus 250 that can be used in place of multi-layer substrate apparatus 110 (shown in FIGS. 1 and 2A). In some embodiments, apparatus 250 includes a first layer 300 that is configured to provide at least one electrical-based property. The electrical-based property can be an electrical conduction source, an electron transfer source, and/or an electrical induction source. For example, as shown in FIG. 2B, first layer 300 can provide electrical inductions, such as ferroelectric and/or pyroelectric behavior. A second layer 302 is positioned proximate to first layer 300. In some embodiments, second layer 302 is configured to provide at least one mechanical-based property, which can include a compliance property, a compactbility property, a rigidity property, and/or a torsional property. For example, in some embodiments, second layer 302 can include a glass material or an allograft material.

In some embodiments, a third layer 304 is positioned proximate to second layer 302, wherein third layer 304 includes at least one chemical component such that third layer 304 is enabled to regulate multi-layer substrate apparatus 250 based, at least in part, on a system, such as system 100, that apparatus 250 is being used with. As such, the chemistry, phase, and composition of third layer 304 can be defined to regulate application-specific behavior. For example, as shown in FIG. 2B, third layer 304 can include an inductive agent, such as an allograft material.

A fourth layer 306 is positioned proximate to third layer 304, wherein fourth layer 306 is configured to provide at least one magnetic-based property. For example, fourth layer 306 can include a metal layer and/or metal component. The metal layer can have a predefined magnetic strength and magnetic response that can be tailored to regulate and respond to application specific processes. For example, the metal layer can be defined based on the system, such as system 100, that apparatus 250 is being used with.

In some embodiments, a fifth layer 308 is positioned proximate to fourth layer 306, wherein fifth layer is configured to provide support based, at least in part, on the system, such as system 100, that multi-layer substrate apparatus 250 is being used with. In some embodiments, fifth layer 308 includes a geometric portion that is configured to facilitate at least one process therein. For example, fifth layer 308 can align architectural form with intended function of apparatus 250 within the system, such as system 100, that apparatus 250 is being used with. Fifth layer 308 can also have, in some embodiments, a mimetic geometry layer for controlling application-specific tasks, and can be configured to adapt and respond to variable environments of the system, such as system 100, that apparatus 250 is being used with. The mimetic geometry layer can include at least one pattern defined thereon and the mimetic geometry can communicate with first layer 300, second layer 302, third layer 304, and/or fourth layer 306.

When apparatus 250 is positioned within a system, such as system 100, first layer 300, second layer 302, third layer 304, fourth layer 306, and/or fifth layer 308 can act autonomously to facilitate and accomplish individual discrete functions, or they can operate cooperatively to regulate multiple interrelated processes. As such, apparatus 250 is a multi-material, multi-interface, multi-functional apparatus that can be pre-programmed for application-specific tasks, and can be designed to adapt and respond to variable environments. Moreover, in some embodiments, there can be interfaces (not shown), or regions between first layer 300, second layer 302, third layer 304, fourth layer 306, and/or fifth layer 308 that can control various processes, such as cell proliferation, differentiation and phenotype expression for stem cell control, infrared photon detection and pyroelectric response for thermal sensors, acoustic and long-wave detection for communication devices, and photon capture and storage for energy-harvesting devices.

Figure 2C:
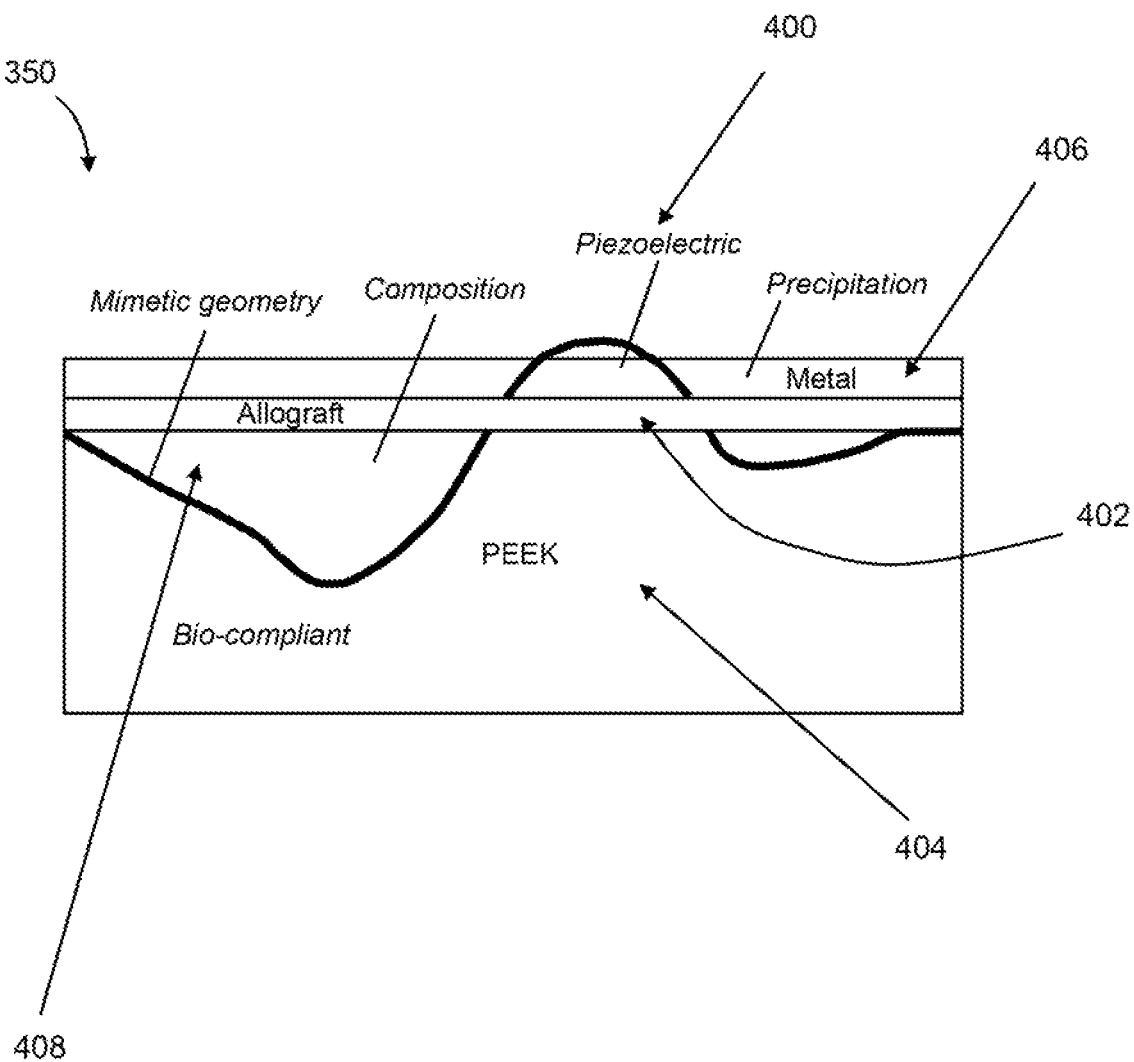
FIG. 2C is a side view of another alternative multi-layer substrate apparatus that can be used with the system shown in FIG. 1, in accordance with some embodiments of the present disclosure.

FIG. 2C is an exemplary side view of an alternative multi-layer substrate apparatus 350 that can be used in place of multi-layer substrate apparatus 110 (shown in FIGS. 1 and 2A). In some embodiments, apparatus 350 includes a first layer 400 that is configured to provide at least one electrical-based property. The electrical-based property can be an electrical conduction source, an electron transfer source, and/or an electrical induction source. For example, as shown in FIG. 2C, first layer 400 can provide electrical inductions, such as piezoelectric behavior and/or pyroelectric behavior. A second layer 402 is positioned proximate to first layer 400. In some embodiments, second layer 402 is configured to provide at least one mechanical-based property, which can include a compliance property, a rigidity property, and/or a torsional property. For example, in some embodiments, second layer 402 can include an allograft material.

In some embodiments, a third layer 404 is positioned proximate to second layer 402, wherein third layer 404 includes at least one chemical component such that third layer 404 is enabled to regulate multi-layer substrate apparatus 350 based, at least in part, on a system, such as system 100, that apparatus 350 is being used with. As such, the chemistry, phase, and composition of third layer 404 can be defined to regulate application-specific behavior. For example, as shown in FIG. 2C, third layer 404 can include an organic thermoplastic polymer, such as a polyetheretherketone.

A fourth layer 406 is positioned proximate to third layer 404, wherein fourth layer 406 is configured to provide at least one magnetic-based property. For example, fourth layer 406 can include a metal layer and/or metal component. The metal layer can have a predefined magnetic strength and magnetic response that can be tailored to regulate and respond to application specific processes. For example, the metal layer can be defined based on the system, such as system 100, that apparatus 350 is being used with.

In some embodiments, a fifth layer 408 is positioned proximate to fourth layer 406, wherein fifth layer 408 is configured to provide support based, at least in part, on the system, such as system 100, that multi-layer substrate apparatus 350 is being used with. In some embodiments, fifth layer 408 includes a geometric portion that is configured to facilitate at least one process therein. For example, fifth layer 408 can align architectural form with intended function of apparatus 350 within the system, such as system 100, that apparatus 350 is being used with. Fifth layer 408 can also have, in some embodiments, a mimetic geometry layer for controlling application-specific tasks, and can be configured to adapt and respond to variable environments of the system, such as system 100, that apparatus 350 is being used with. The mimetic geometry layer can include at least one pattern defined thereon and the mimetic geometry can communicate with first layer 400, second layer 402, third layer 404, and/or fourth layer 406.

When apparatus 350 is positioned within a system, such as system 100, first layer 400, second layer 402, third layer 404, fourth layer 406, and/or fifth layer 408 can act autonomously to facilitate and accomplish individual discrete functions, or they can operate cooperatively to regulate multiple interrelated processes. As such, apparatus 350 is a multi-material, multi-interface, multi-functional apparatus that can be pre-programmed for application-specific tasks, and can be designed to adapt and respond to variable environments. Moreover, in some embodiments, there can be interfaces (not shown), or regions between first layer 400, second layer 402, third layer 404, fourth layer 406, and/or fifth layer 408 that can control various processes, such as cell proliferation, differentiation and phenotype expression for stem cell control, infrared photon detection and pyroelectric response for thermal sensors, acoustic and long-wave detection for communication devices, and photon capture and storage for energy-harvesting devices.

Figure 3:
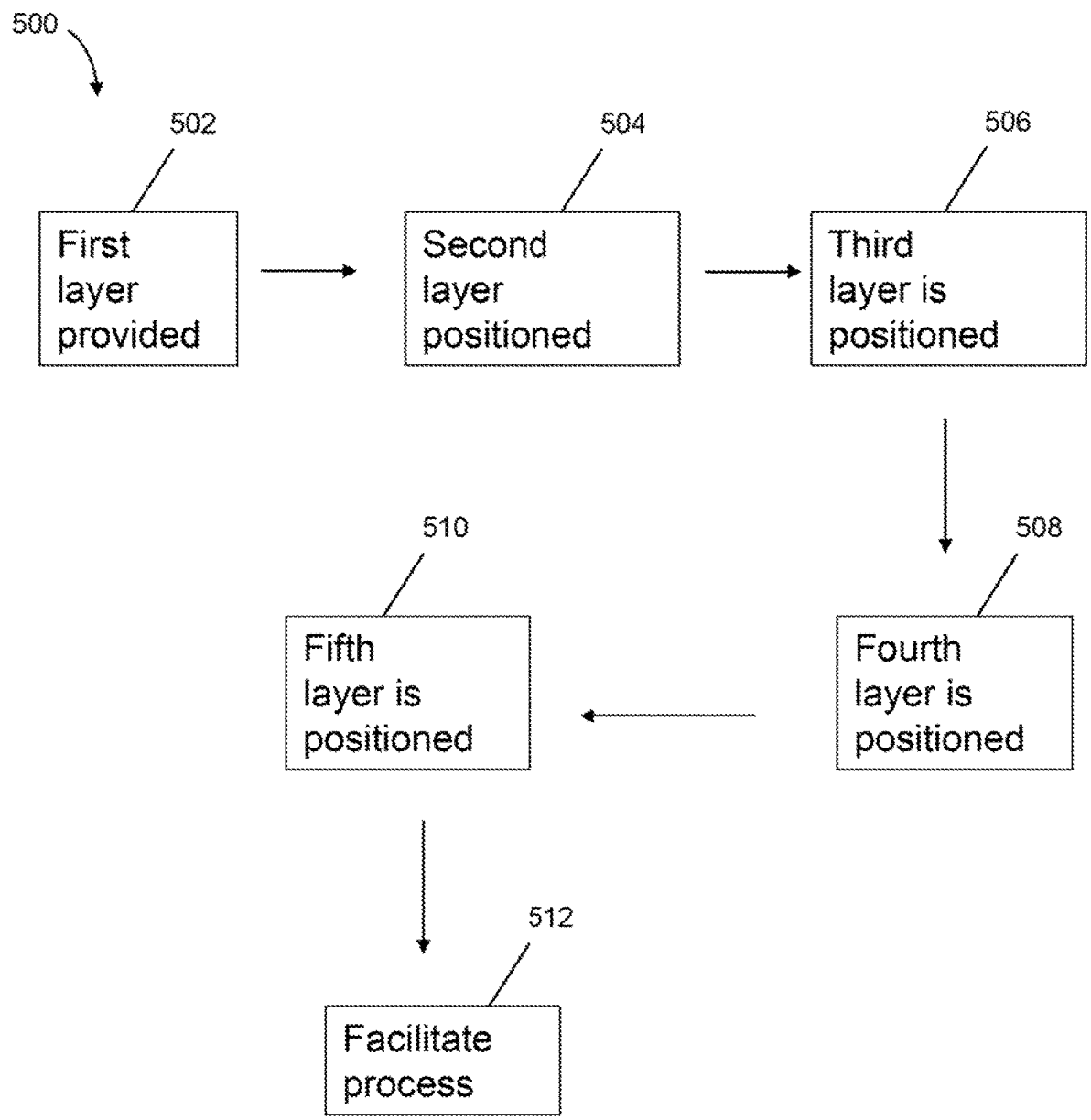
FIG. 3 is a flow diagram of an exemplary method that can be used to assemble the multi-layer substrate apparatus shown in FIG. 3A, in accordance with some embodiments of the present disclosure.

FIG. 3 is a flow diagram 500 of an exemplary method of assembling a multi-layer substrate apparatus, such as multi-layer substrate apparatus 110 (shown in FIGS. 1 and 2A). In step 502, a first layer, such as first layer 200 (shown in FIG. 2A), is provided, wherein the first layer is configured to provide at least one electrical-based property. In step 504, a second layer, such as second layer 202 (shown in FIG. 2A), is positioned proximate to the first layer, wherein the second layer is configured to provide at least one mechanical-based property. In step 506, a third layer, such as third layer 204 (shown in FIG. 2A), is positioned proximate to the second layer, wherein the third layer includes at least one chemical component such that the third layer is enabled to regulate the multi-layer substrate apparatus based, at least on part, on a system, such as system 100 (shown in FIG. 1), that the apparatus is being used with. In step 508, a fourth layer, such as fourth layer 206 (shown in FIG. 2A), is positioned proximate to the third layer, wherein the fourth layer is configured to provide at least one magnetic-based property. In step 510, a fifth layer, such as fifth layer 208 (shown in FIG. 2A), is positioned proximate to the fourth layer, wherein the fifth layer is configured to provide support based, at least in part, the system that the multi-layer substrate is being used with. In step 512, at least one process is facilitated and/or performed within the fifth layer using a geometric portion defined within the fifth layer.

In some embodiments, fabricating apparatus, such as multi-layer substrate apparatus 110, can require known sophisticated material-specific fabrication, structuring and activation capabilities that extend from the micro- to the nanoscale domains, and may provide exquisite patterning, phase and energetic control. For example, in some embodiments, laser-scripted pulse sequencing techniques can be used that permit the delivery of discrete laser energy packets—in the form of pulse scripts—into implant materials for creating advanced biomimetic polylaminate architectures. Systems and methods for performing such techniques are described in co-pending U.S. patent application Ser. No. 15/469,132 entitled SYSTEMS AND METHODS FOR MODIFYING MATERIAL SUBSTRATES filed Mar. 24, 2017, which is a continuation in part of and claims priority to U.S. patent application Ser. No. 14/163,712 entitled MATERIAL MODIFICATION ASSEMBLY AND METHOD FOR USE IN THE MODIFICATION OF MATERIAL SUBSTRATES filed Jan. 24, 2014, which is a continuation-in-part of and claims priority to U.S. patent application Ser. No. 13/767,055 entitled BONE GROWTH ENHANCING IMPLANT filed Feb. 14, 2013 and issued as U.S. Pat. No. 8,679,189 on Mar. 25, 2014, which claims the benefit of U.S. Provisional Application 61/763,223, filed Feb. 11, 2013, the disclosures of which are incorporated herein by reference in their entirety.

Using such laser genotype pulse-scripting technology, laser pulse sequences (process scripts) are linked on a line-by-line fashion to the toolpath and machining code (pattern scripts) to ensure the delivery of discrete pulse sequences to a substrate material on a spot-by-spot basis. The pulse sequences can be predefined and are derived from the underlying chemical physics, solid-state dynamics and photochemistry associated with the laser-material interactions. The respective pulses in a sequence or script can be modulated in amplitude (intensity), pulse duration (pulse width), frequency (repetition rate) and polarization (electric-field orientation), or any combination thereof. The specialized material processing capabilities are not attainable with traditional approaches and do not currently exist in the commercial or industrial sectors.

The fabrication and elaboration of structures and phases intended for polylaminate applications can be illustrated through the laser tailoring of the commonly employed biomaterials, such as authentic bone, organic thermoplastics, and metallic substrates, wherein these material systems are appropriately represented by human allografts (cortical bone), polyether-ether-ketone and bulk metallic glasses. While the examples presented in this disclosure involve materials tailoring and biological encoding through laser-mediated processes, similar transformations and activations can be achieved through other energy-based mechanisms, such as X-ray, electron beam, ultrasonics, and three-dimensional manufacturing.

The embodiments described herein correspond to the ability to fabricate multi-constituent, multi-phase implant structures and interbody architectures, such as multi-layer substrate apparatus 110, based on polylaminate material differentiation platforms. In some embodiments, the structures and features of apparatus 110 are reminiscent of natural biological forms, capable of controlling various phases of cell-surface interactions, cell efficacy and device integration. The embodiments described herein combine hybrid material systems and laser-modified chemical and physical structuring to prepare engineered inhomogeneities or compositional inclusions with multiple functionalities. Apparatus 110 is hierarchical in design, and graded in structure, composition and function. Instead of a single material construct with singular function, the apparatus 110 provides a cooperative network of materials, structures, inductions and conductions that can adapt, respond and regulate, for example, human physiology at the cell level. Apparatus 110 can adapt to any type of system it is being used with.

Apparatus 110 corresponds to systems that combine organic materials, inorganics-ceramics, metals and allografts. As described above, apparatus 110 includes laminates of, for example, bioglass/tricalcium phosphate/hydroxyapatite, bioglass/allograft and metal/allograft/polyetheretherketone. These materials retain inherent versatility, combining biocompatibility and inductive-conductive capacity ascribed by their chemical compositions and physical properties. The individual discrete layers (electrical/mechanical/chemical/magnetic/structure-geometry) can be repeated and/or duplicated in any order, and their sequencing and frequency can be interchanged to enable apparatus 110 to function as described herein. In some embodiments, such as an implant device or interbody device, one individual discrete layer can provide instructions or affect the processes occurring at one or more of the other layers that comprise the apparatus 110 and allow it to function as described herein. For example, a layer that provides an electrical-based property, like piezoelectric behavior, can generate electrical current in response to a compression or loading force. This electrical current can then stimulate the attachment of cells on one or more of the other layers, thereby controlling and improving tissue ingrowth and fixation of the implant or interbody device to enable apparatus 110 to function as described herein.

Exemplary embodiments of the apparatus, systems, and methods are described above in detail. The apparatus, systems, and methods are not limited to the specific embodiments described herein, but rather, components of the apparatus, systems, and/or steps of the method may be utilized independently and separately from other components and/or steps described herein. For example, the apparatus may also be used in combination with other systems and methods, and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A multi-layer substrate apparatus comprising:
   a first layer configured to provide at least one electrical-based property;
   a second layer positioned proximate to said first layer, wherein said second layer is configured to provide at least one mechanical-based property;
   a third layer positioned proximate to said second layer, wherein said third layer comprises at least one chemical component such that said third layer is enabled to regulate said multi-layer substrate apparatus based, at least in part, on a system that said multi-layer substrate apparatus is being used with;

a fourth layer positioned proximate to said third layer, wherein said fourth layer is configured to provide at least one magnetic-based property; and a fifth layer positioned proximate to said fourth layer, wherein said fifth layer is configured to provide support based, at least in part, on the system that said multi-layer substrate apparatus is being used with, wherein said fifth layer further comprises a geometric portion that is configured to facilitate at least one process therein.

2. A multi-layer substrate apparatus in accordance with claim 1, wherein the at least one electrical based property is an electrical induction source.

3. A multi-layer substrate apparatus in accordance with claim 2, wherein the electrical induction source includes at least one of a ferroelectric component, a piezoelectric component, or a pyroelectric component.

4. A multi-layer substrate apparatus in accordance with claim 1, wherein the at least one mechanical-based property includes at least one of a compliance property, a compactbility property, a rigidity property, or a torsional property.

5. A multi-layer substrate apparatus in accordance with claim 1, wherein the at least one chemical component includes at least one of a chemical property, a phase property, or a composition property.

6. A multi-layer substrate apparatus in accordance with claim 1, wherein the at least one magnetic-based property includes at least one of a magnetic strength property, a magnetic response property, or a magnetic orientation property.

7. A multi-layer substrate apparatus in accordance with claim 1, wherein said geometric portion comprises at least one pattern defined thereon.

8. A multi-layer substrate apparatus in accordance with claim 1, wherein said geometric portion is configured to communicate with at least one of said first, second, third, and fourth layers.

9. A system comprising:
at least one portion comprising a cavity defined therein; and
a multi-layer substrate apparatus positioned in said cavity, wherein said multi-layer substrate comprises:
a first layer configured to provide at least one electrical-based property;
a second layer positioned proximate to said first layer, wherein said second layer is configured to provide at least one mechanical-based property;
a third layer positioned proximate to said second layer, wherein said third layer comprises at least one chemical component such that said third layer is enabled to regulate said multi-layer substrate apparatus based, at least in part, on said at least one portion;
a fourth layer positioned proximate to said third layer, wherein said fourth layer is configured to provide at least one magnetic-based property; and
a fifth layer positioned proximate to said fourth layer, wherein said fifth layer is configured to provide support based, at least in part, on said at least one portion, said fifth layer further comprises a geometric portion that is configured to facilitate at least one process therein.

10. A system in accordance with claim 9, wherein the at least one electrical-based property is an electrical induction source.

11. A system in accordance with claim 10, wherein the electrical induction source includes at least one of a ferroelectric component, a piezoelectric component, or a pyroelectric component.

12. A system in accordance with claim 9, wherein the at least one mechanical-based property includes at least one of a compliance property, a compactbility property, a rigidity property, or a torsional property.

13. A system in accordance with claim 9, wherein the at least one chemical component includes at least one of a chemical property, a phase property, or a composition property.

14. A system in accordance with claim 9, wherein the at least one magnetic-based property includes at least one of a magnetic strength property, a magnetic response property, or a magnetic orientation property.

15. A system in accordance with claim 9, wherein said geometric portion comprises at least one pattern defined thereon.

16. A system in accordance with claim 9, wherein said geometric portion is configured to communicate with at least one of said first, second, third, and fourth layers.

17. A method of assembling a multi-layer substrate apparatus, said method comprising:
providing a first layer that is configured to provide at least one electrical-based property;
positioning a second layer proximate to the first layer, wherein the second layer is configured to provide at least one mechanical-based property;
positioning a third layer proximate to the second layer, wherein the third layer comprises at least one chemical component such that the third layer is enabled to regulate the multi-layer substrate apparatus based, at least in part, on a system that the multi-layer substrate apparatus is being used with;
positioning a fourth layer proximate to a third layer, wherein the fourth layer is configured to provide at least one magnetic-based property; and
positioning a fifth layer proximate to the fourth layer, wherein the fifth layer is configured to provide support based, at least in part, on the system that the multi-layer substrate apparatus is being used with; and
facilitating at least one process within the fifth layer using a geometric portion defined within the fifth layer.

18. A method in accordance with claim 17, wherein the at least one electrical-based property is an electrical induction source.

19. A method in accordance with claim 18, wherein the electrical induction source includes at least one of a ferroelectric component, a piezoelectric component, or a pyroelectric component.

20. A method in accordance with claim 17, wherein the at least one mechanical-based property includes at least one of a compliance property, a rigidity property, or a torsional property.

21. A method in accordance with claim 17, wherein the at least one chemical component includes at least one of a chemical property, a phase property, or a composition property.

22. A system in accordance with claim 17, wherein the at least one magnetic-based property includes at least one of a magnetic strength property, a magnetic response property, or a magnetic orientation property.

23. A method in accordance with claim 17, wherein the geometric portion includes at least one pattern defined thereon.

* * * * *